(12) United States Patent
Bromer

(10) Patent No.: US 6,986,208 B1
(45) Date of Patent: Jan. 17, 2006

(54) BLADE WITH MICROSCOPIC CERAMIC CUTTING PLATES

(76) Inventor: Nicholas S. Bromer, 5713 Namakagan Rd., Bethesda, MD (US) 20816

( * ) Notice: Subject to any disclaimer, the term of this patent is extended or adjusted under 35 U.S.C. 154(b) by 468 days.

(21) Appl. No.: 09/708,658

(22) Filed: Nov. 9, 2000

Related U.S. Application Data

(60) Provisional application No. 60/164,556, filed on Nov. 10, 1999.

(51) Int. Cl.
*B26B 9/00* (2006.01)

(52) U.S. Cl. .......................................... 30/350; 30/357

(58) Field of Classification Search .................. 30/350, 30/357, 346.54, 346.55; 428/408, 410, 621, 428/627, 432, 698, 699; 451/901, 45
See application file for complete search history.

(56) References Cited

U.S. PATENT DOCUMENTS

| | | | | |
|---|---|---|---|---|
| 1,607,083 A | * | 11/1926 | Ignatieff | 76/115 |
| 2,555,214 A | * | 5/1951 | Wallach et al. | 216/53 |
| 3,543,402 A | * | 12/1970 | Seager | 30/346.53 |
| 3,652,342 A | * | 3/1972 | Fischbein et al. | 148/277 |
| 3,754,329 A | * | 8/1973 | Lane | 30/346.53 |
| 3,894,337 A | * | 7/1975 | Jones | 30/346.54 |
| 3,911,579 A | * | 10/1975 | Lane et al. | 204/192.15 |
| 4,653,373 A | * | 3/1987 | Gerber | 30/350 |
| 4,933,058 A | * | 6/1990 | Bache et al. | 204/192.15 |
| 4,991,481 A | | 2/1991 | Gerber | |
| 5,077,901 A | * | 1/1992 | Warner et al. | 30/346.53 |
| 5,214,011 A | * | 5/1993 | Breslin | 30/346.54 |
| 5,232,568 A | * | 8/1993 | Parent et al. | 204/192.15 |
| 5,431,071 A | * | 7/1995 | Williams | 30/350 |
| 5,435,815 A | * | 7/1995 | Ikegaya et al. | 51/295 |
| 5,477,616 A | | 12/1995 | Williams et al. | |
| 5,549,604 A | * | 8/1996 | Sutcu et al. | 606/39 |
| 5,630,275 A | * | 5/1997 | Wexler | 30/50 |
| 5,724,868 A | | 3/1998 | Knudsen et al. | |
| 6,293,020 B1 | * | 9/2001 | Julien | 30/346.53 |
| 6,330,750 B1 | * | 12/2001 | Meckel | 30/346.54 |
| 6,431,800 B1 | * | 8/2002 | Suzuki | 407/119 |

OTHER PUBLICATIONS

Carr et al., Subsurface Structure in Polished Fused Silica and Diamond Turned Single Crystal Silicon, Jun. 1999.*
"Roughness Height Table" in Machinery's Handbook 26th Edition, p. 703.*
Bennett & Mattsson, Surface Roughness and Scattering Ott. Society of Am.
Modern Grinding Process Technology by Salmon.
Burkart/Schmotz, Grinding & Polishing Theory and Practice.
Burkart, Silman and Draper, Mechanical Polishing.

* cited by examiner

*Primary Examiner*—Boyer D. Ashley

(57) ABSTRACT

A blade has a hard, thin layer of ceramic on one side, so that when the blade is sharpened on the other side the very hard ceramic is disposed at the cutting edge. The ceramic (for example, TiN) may be deposited by vacuum deposition. The surface onto which the ceramic is deposited is specular (mirror-like), so that it is flat or smooth on the order of a wavelength of light. The ceramic layer, which is very thin, takes the form of a flat plate, when viewed on a microscopic scale. The ceramic forms a cutting plate at the edge of the blade.

6 Claims, 2 Drawing Sheets

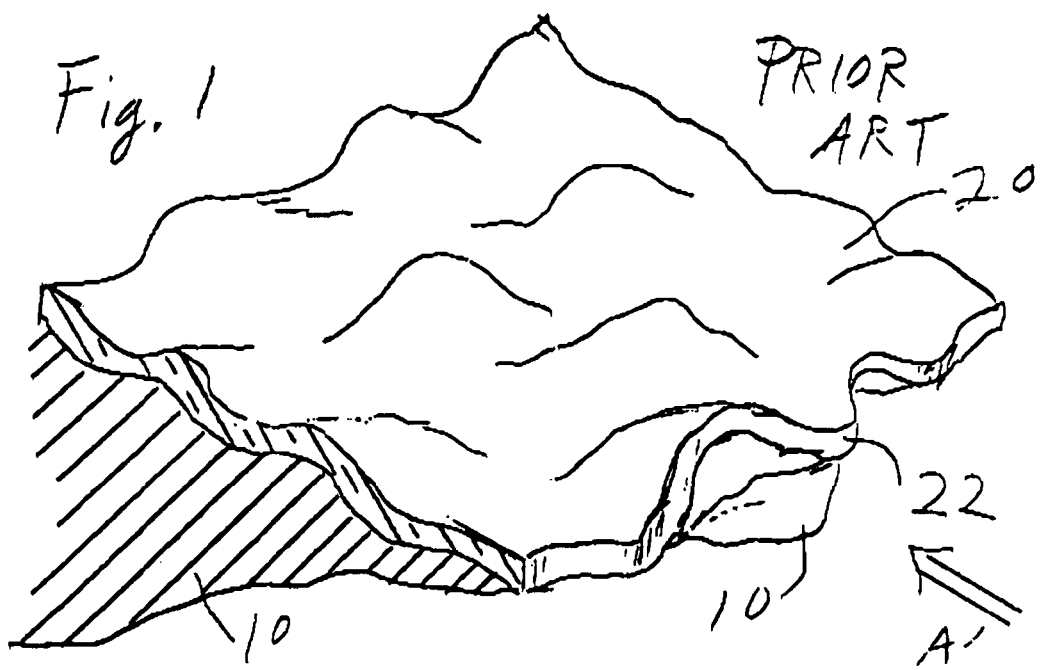
Fig. 1 PRIOR ART
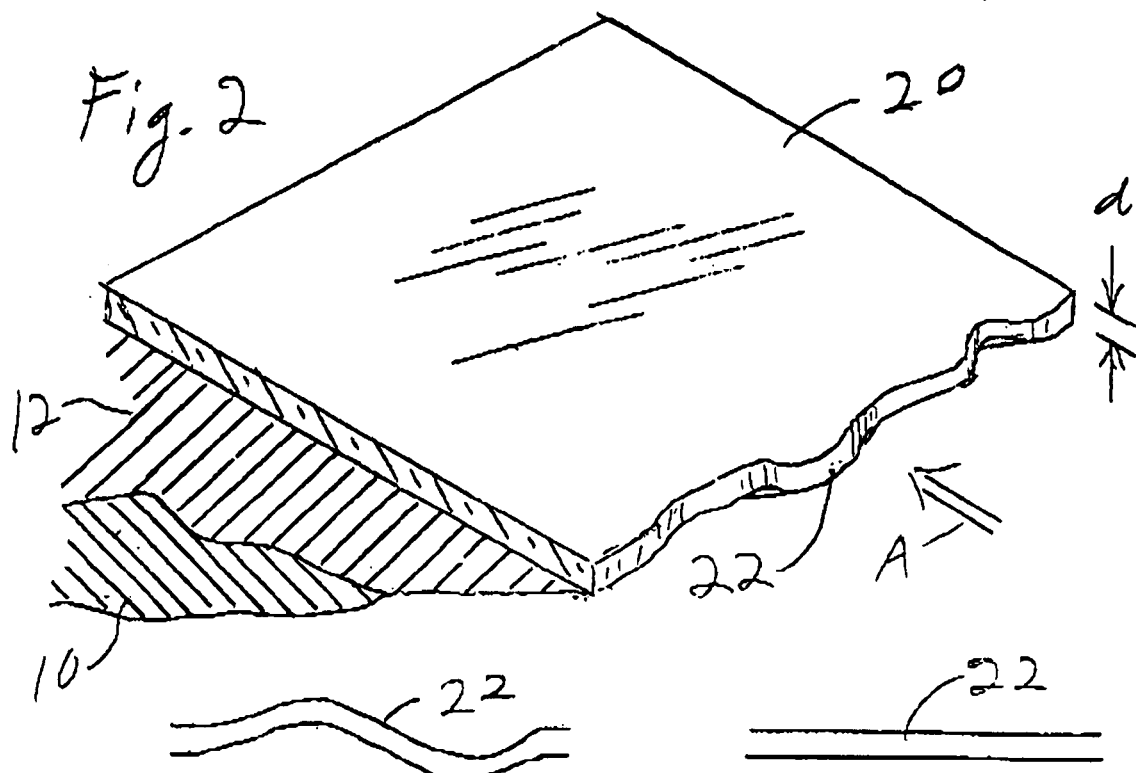
Fig. 2
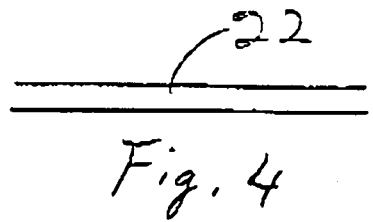
Fig. 3 PRIOR ART
Fig. 4

BLADE WITH MICROSCOPIC CERAMIC CUTTING PLATES

CROSS-REFERENCE TO RELATED APPLICATION

This application claims the benefit of provisional utility patent application Ser. No. 60/164,556, filed Nov. 10, 1999 by the same applicant.

FIELD OF THE INVENTION

The present invention relates to cutting blades, such as knives or razors, having a thin hard layer on one side.

REVIEW OF RELATED TECHNOLOGY

Knife blades are always ground flat on the surface next to the cutting edge. One of the two surfaces next to the edge may be scalloped (a "serrated" blade), but even in the case of a "flamed" sword there is always one viewing direction in which the cutting edge appears as a straight line. Another way of saying this is that the edge is always straight in the cutting direction.

A non-straight cutting edge would be inefficient. First, slicing motion of such a blade would create a sawing action, rather than a cutting action, in the portions of the cutting edge at an angle to the slicing direction of motion. The angled portions of the edge, moving sideways, would scrape rather than cut and would create high friction. Second, when pushing the edge straight into the material (without slicing), the length of the cut would be longer because a sinuous line is longer than a straight line. For these reasons no blade is made anything but straight in the cutting direction.

On the microscopic scale, however, ridges and valleys are left by sharpening stone grit and the edge is anything but straight. This creates cutting inefficiency on a scale too small to see.

The present invention relates to this lack of microscopic straightness, and its relation to blade coatings of hard materials such as ceramic.

U.S. Pat. No. 5,724,868 to Knudsen et al discloses a cutting blade made of ordinary metal (400 series stainless steel) with a thin layer of a hard ceramic, such as TiN, layered onto one side of the blade. The blade is sharpened only on the side opposite the ceramic, placing the thin layer of very hard ceramic material at the cutting edge. Because the edge is thus made very hard, the cutting edge dulls very slowly, and Knudsen presents graphs of experimental results showing greatly increased edge life.

U.S. Pat. No. 5,477,616 to Williams et al shows a very thin (2 μm to 20 μm thick) hard layer on a steel blade. U.S. Pat. No. 4,991,481 to Gerber discloses a blade with a hard layer on one side.

The ceramic layers' thicknesses are on the order of a μm (micron or micrometer, one millionth of a meter or a thousandth of a millimeter: in English measure, about 0.04 of one thousandth of an inch or 0.04 mil). Knudsen's ceramic layer is 1.5 to 5 μm and Williams' is 8–15 μm. These thicknesses are several times a wavelength of light, which is about 5000 Angstroms or 0.5 μm (visible light ranges from 4000 to 7000 Angstroms in wavelength).

The surface roughness of a sharpened blade—the average depth of the microscopic valleys—is longer than a wavelength of light, as is shown by the fact that the surface of a sharpened knife blade is not "specular", that is, not image-reflecting like a speculum (mirror). If the surface were flat or smooth on the scale of a light wavelength, the knife would be specular and mirror images would be visible in it.

Ordinary sharpening stones are too rough to polish a surface, i.e. make it specular. Very fine number 60 grit has a diameter of 275 μm (55 times the thickness of a typical thick ceramic layer and about 500 times a light wavelength) and the gouges it leaves on a knife blade are probably of the same order of magnitude.

FIG. 1, labeled "Prior Art", shows in a microscopic view a ceramic layer 20' which is convoluted because of being deposited onto the convoluted rough surface of a metal blade 10'.

When this blade is sharpened on the opposite side, the ceramic layer 20' will be abraded or broken off at or near the apex of the cutting edge. Since the ceramic layer 20' is not flat, the edge 22' of the ceramic layer 20' will not be straight in the cutting direction. On the microscopic scale, along a line of sight in the direction of the arrow A in FIG. 1, it will appear as in FIG. 3.

It has been found that a ceramic layer not only keeps a blade sharp longer, but it can even cause the blade to become sharper with use. This is discussed in the Knudsen patent. The probable reason is that the harder ceramic layer is left behind when the softer metal is rubbed away by the material being cut. For example, a ceramic-coated blade with a cutting edge roughly squared-off should become triangular as the metal wears away from the side without ceramic.

However, the self-sharpening effect noted by Knudsen does not achieve great sharpness. Most likely, the edge of the ceramic layer is not straight in the cutting direction. With adjoining metal worn away, the edge is erratic in the cutting direction and its angle of attack varies. Pieces at an angle may break off from the large force of cutting. Depending on the deposition method, the thickness of the ceramic layer may also vary, leading to additional breakage at weak points and further irregularity.

The convolutions of the ceramic coating reduce the sharpness below what is possible.

A door kick plate (rectangular plate with screw holes intended to be fastened at the bottom of a door), made by the Baldwin company and available in stores, is made of polished stainless steel coated with ceramic.

SUMMARY OF THE INVENTION

To increase the sharpness of a ceramic-coated blade or razor, the present invention layers the hard ceramic onto a surface so flat or smooth that it is specular (mirror-like). When coated with ceramic, the ceramic layer is thin and flat on the order of a wavelength of light, i.e. on the order of a half a micron (μm). The flat plate of hard ceramic acts as a cutting edge when the adjoining metal is worn away. Because the edge is straight, cutting efficiency (sharpness) is increased.

The sharpness that can be obtained with a specular surface is demonstrated by the fact that fractured-glass microtome blades are sharper than metal microtome blades. The surface of broken glass is specular (this is evident just from looking at a piece of broken glass). But glass is of course too brittle for knives and razors, the edge is difficult to shape, and glass edges dull themselves in only a few hours because of surface tension. Glass is a very viscous liquid, not a crystal solid, and it will gradually flow.

The flow of a liquid under the force of surface tension always reduces the surface area, and therefore a projecting portion of liquid (such as a point or edge in glass) will be pulled back in.

Therefore, the liquid nature of glass can be used to create a specular surface. When glass is hot, its viscosity is reduced and it flows as fast as honey. In this state, any irregularities in the surface will rapidly be pulled down by surface tension, and a rough surface (which is really just microscopic projecting points and ridges) will smooth itself, and become specular.

In particular, a thin coating of hot glass on a rough surface will flow to make a smooth outer glass surface, just as cold honey spread over a piece of hot toast will quickly become smooth and specular.

If a sheet of rough-surfaced material like stainless steel is coated with glass powder and then heated (or sprinkled with glass powder while hot), after some time the glass will cover the surface, form a sheet, and smooth its outer surface into a specular surface. The surface irregularities will be filled in on the metal side, while the outer surface or air side of the glass will become smooth and specular through surface tension. When cooled, the glass will become very hard.

As noted above, glass is quite brittle and cannot be used, alone, for a blade. But glass is actually a very strong material, stronger than steel under ideal conditions. Glass breaks easily because surface cracks in the glass grow under stress and grow bigger. This is demonstrated by the fact that, when the surface of glass is specially smoothed, the glass is much stronger. One way to do this is by "fire-polishing", heating the glass and letting surface tension remove the cracks.

In the present invention, a thin coating of glass, made specular by heating, is coated with a very thin ceramic plate, which is harder than glass and acts as a cutting edge. The specular glass surface results in a specular ceramic coating, flat on a microscopic scale. The ceramic not only increases the hardness at the cutting edge, it also prevents the glass edge from flowing itself dull from surface tension: the ceramic is a true solid and will not flow; it stays flat. As long as the glass "wets" the ceramic (adheres to it), the glass will not retreat from the edge of the ceramic plate and the edge will not become dull from surface tension.

The ceramic also protects the glass surface and reduces the number of scratches, which weaken the glass.

Preferably, the glass is selected to have a coefficient of thermal expansion comparable to that of the underlying metal or other substrate material, and the substrate material surface is treated, if need be, to insure that the glass adheres well. If the adhesion is strong, then if the glass layer cracks for any reason the glass will not flake off and the cutting ability of the blade will not be impaired.

Another way that the present invention creates a specular surface is by mechanical polishing or electro-polishing, or preferably, by chromium plating. The ceramic coating is laid more or less uniformly over the polished surface, flat and smooth on a microscopic scale, creating a microscopic flat ceramic plate which is straight in the cutting direction. This produces a sharper blade.

To optimize the sharpness of the blade, the cutting layer should be smooth (locally flat) on a distance scale less than or generally equal to its thickness. If the corrugations in the cutting layer are much deeper than the cutting layer is thick, then the cutting layer will not present a thin layer that lies in the direction of cutting. The edge cannot be the intersection two planes, and therefore cannot be sharp.

BRIEF DESCRIPTION OF THE DRAWING FIGURES

FIG. 1 is a perspective view of a prior-art knife edge.

FIG. 2 is a perspective view of the knife edge of the invention.

FIG. 3 is an edge-on view of the knife edge of FIG. 1.

FIG. 4 is an edge-on view of the knife edge of FIG. 2.

DETAILED DESCRIPTION OF THE PREFERRED EMBODIMENT

Figure 6:
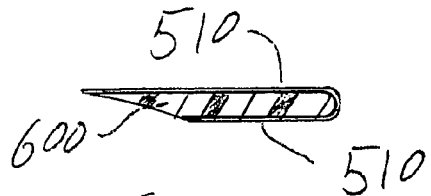
FIG. 6 is a cross-sectional view of the blade made by the method of FIG. 5.

Here, and in the following claims:

"specular" means that at least some reflected image is visible on a surface, but does not mean that the surface is polished or mirror-like—any surface on which any reflected image is at all visible is specular, and distortion in that image, no matter how much, will not prevent the surface from being "specular";

"ceramic" means any hard, solid, or crystalline material.

"bonded" means joined by mechanical fastening, by adhesive, by vapor or chemical deposition of one layer onto another, or by any other means;

"dissimilar" means two materials having respective compositions so unlike that they cannot be joined by welding;

"light" means visible light, ultraviolet light, and infrared light (near infrared and far infrared), by which images can be reflected in a specular fashion;

"on the order of" means within a factor of ten (e.g. a centimeter is on the order of 1.1 millimeters and also on the order of 9.9 centimeters;

"polishing" includes any process, whether mechanical, electrical, chemical, thermal, or of any other nature whatsoever, which coverts a non-specular surface into a specular surface.

FIG. 2 shows the present invention. The ceramic coating layer 20 is deposited on a knife blade 10, preferably of hard metal, glass, or glassy material, which is smooth enough that light is reflected and an image is visible in the reflection (assuming the material reflects sufficient light). The outer ceramic surface is generally flat and a reflected image may be visible either on the outer surface of the ceramic or from the metal or glass surface beneath, when the ceramic is transparent.

The surface on which the ceramic 20 is coated may be mechanically polished, electro-polished, or otherwise polished, for example by liquid flow or melting. Preferably an ordinary non-specular blade (or a portion near the edge) is plated with a secondary coating layer 12 which has a specular outer surface due to the plating or polishing process and needs no further polishing. One example is chromium plating, which is applied via a widely-used process.

The cutting edge is formed and/or sharpened by abrading the side of the blade opposite to the ceramic 20. When an ordinary grinding stone has sharpened the blade, the edge it will be irregular as viewed from the side, like a microscopic serrated edge. But in the edge-on view parallel to the surface of the ceramic layer 20 (in the direction of arrow A of FIG. 2), it will appear straight.

To optimize sharpness the plate 20 should be smooth (locally flat) on a distance scale generally equal to, and preferably less than, its thickness. If the surface is specular it is also smooth to less than a wavelength of light, which is about 0.5 $\mu$m. (A high-quality optical mirror is flat to one-quarter wave, but locally smooth to better than that. Overall flatness is not essential for the present invention, but smoothness or local flatness permits the coating to be plate-like.) A ceramic layer about 1 µm thick coated onto a specular surface will form a substantially uniform flat plate 20 as illustrated.

The plate 20 preferably is so thin that it acts as a cutting layer even when the ceramic plate 20 is not beveled, e.g. when the plate 20 has broken off above the metal 12. The plate thickness "d" shown in FIG. 2 is chosen such that the blade is sufficiently sharp even without any beveling of the ceramic plate 20. A ceramic plate with a thickness approaching 1 µm (1000 Angstroms) corresponds to the edge of a very sharp razor.

Ordinary sharpening on the side of the blade opposite the plate 20, in a direction angled to the edge, will leave corrugations or ridges in the metal and undulations in the edge of the ceramic plate 20 (as viewed from the side, not along the arrow A). Sharpness will not be decreased, because the edge of the ceramic plate 20 is (on a microscopic scale) serrated, but is still straight in the cutting direction and it will still move straight into the cut.

The sharpness of the ceramic-plate cutting edge may be increased by polishing the side opposite to the plate 20 or by removing the metal 12 or 10 from the region just adjacent the plate edge. Doing this will effectively increase the edge angle right at the edge. If the metal should be removed far back from the edge, the ceramic plate may break off under the force of cutting. However, this might not be a disadvantage because the projecting edge will still be sharp.

The invention contemplates several ways of removing metal near the cutting edge of the plate 20. One is corrosion, for example, acid etching. If a thin layer of metal is removed from the side not shielded from chemical action by the ceramic plate, the edge of the plate will be exposed and the edge will be sharpened.

An alternate method is electro-etching. By applying a voltage to the metal while the blade is immersed in a suitable solution, metal can be removed under the influence of the applied voltage. Electro-etching would only dull an ordinary knife because the electric field, which controls the rate of metal removal, reaches very high values at a projections such as point or ridge, and therefore the metal is removed faster at the edge of a blade than it is elsewhere. In the ceramic-plate edge of this invention, though, electro-etching is ideal for exposing a little bit of the ceramic edge. The metal 12 or 10 will be removed most quickly right at the edge, so that only a very brief period of electro-etching would be required to sharpen the blade.

Combinations of chemical, electrochemical, and abrasive metal removal may give optimum results.

In the case where the secondary coating layer 12 is made of glass or other glassy material, abrasion is the preferred method. However, secondary heating of the sharpened edge can at least partially smooth the rough, abraded side of the cutting edge opposite the ceramic plate 20, resulting in a cutting edge with less friction and an easier cut. Microscopic ridges and valleys will tend to flow into a smooth surface when the glass becomes less viscous.

The edge could also become sharper due to secondary heating after the edge is sharpened by abrasion, because the glass will form a "meniscus" whose shape depends on the wetting of the ceramic plate by the glass. Liquid water forms beads on some surfaces, which the water does not wet, such as wax paper, and spreads out over other surfaces, such as very clean glass. "Wetting" describes the adhesion of a liquid to a solid; it is caused by the same forces of molecular attraction as those which make glue work.

If the glass 12 does wet the plate 20 when it is brought to a flowing liquid state by heat, the glass will tend to bead up like water on wax paper, and the edge will become rounded; this is not the type of meniscus desired for a hollow edge (although it might be desirable where the edge is to be made mechanically stronger at the cost of sharpness). But if the glass wets the plate 20 and adheres to it, then the plate will pull on the glass and stretch it out along the direction A, causing the edge to become sharper.

In order to form a good bond between the glass 12 and the ceramic plate 20, the glass should be very clean when the ceramic is deposited. Also, chemical treatment to increase or otherwise improve the adherence of the plate 20 to the glass 12 is part of the invention.

The thickness of the glass layer is preferably small for blades which need to be tough. But the present invention contemplates a blade made entirely of glass for applications such as microtomes.

The present invention is expected to be self-sharpening because the hard ceramic plate 20 will be worn away more slowly than the adjoining material 12 or 10, which is preferably softer. Unlike previous prior-art ceramic-coated blades, in the invention the major component of cutting force is aligned with the plate, so that the plate edges will fail by buckling (compression). In the prior-art blades the ceramic layer is apt to be at any angle to the cut and is likely to fail by bending. A plate will bend and break under a much smaller force than is required to buckle the plate from a force applied edge-on, especially when the plate is supported by the substrate material 10 or 12.

If the ceramic plate 20 is thin enough, then the invention is expected to be sharper than an ordinary knife or razor. In general, it is well-known that a soft material will not take or keep an edge, and that harder materials such as ceramic and chromium are better. An ordinary blade can be sharpened by polishing, but it cannot be as sharp as the ceramic plate of the invention because the large force at the edge will distort the metal, bending the edge over. It is believed that the reason why blades are stropped is to break off the edge "feather" caused by plastic flow of the metal under the very large forces present at the edge during conventional sharpening.

Even greater sharpness can be achieved if the ceramic plate 20 is beveled to a cross-sectional apex. After the glass or metal 10 and 12 is removed sufficiently, then a very fine and very hard abrasive could be used to "sharpen" the ceramic. Such a beveled ceramic plate 20 might be used for a microtome. A beveled ceramic plate could combine great sharpness with a thick, tough ceramic layer.

The ceramic plate 20 is preferably formed directly onto the specular surface of the substrate 10 or 12, preferably by vapor or ion deposition or implantation or some other commercially available method. One preferred material is TiN. Another is diamond.

Especially in the embodiments using a glassy specular surface, when the underlying substrate 10 has surface roughness including parallel ridges and valleys, such as might be produced from unidirectional sanding or wire-brushing, the invention contemplates aligning the ridges and valleys more or less perpendicular to the cutting edge. This creates a complementary pattern of ridges on the undersurface of the layer 12, which strengthen the edge.

The invention includes a process of making the blade described above.

The specularity of a surface is not only a structural aspect of the present invention (because a specular blade has increased sharpness); it is also a convenient test of the smoothness/flatness of a surface. Looking at a surface, either with the naked eye or through an optical device (for example, a microscope), is a rapid and inexpensive step in a process of making a very sharp blade with at least one specular surface. Moreover, the human eye can also immediately detect the quality of such a surface. For example, a surface with a finely scratched or pitted smooth surface can be seen as a "clouded" mirror surface in which the image is clear but faint.

In the case of the one preferred embodiment in which the layer 12 is chromium or other hard metal, the invention includes (among other methods), timed plating of the substrate 10 in a plating apparatus, and it also includes human visual inspection of the plated surface to determine when the surface has become specular, and it also includes automatic or partially automatic inspection by equipment using optics and/or image processing to make the same determination as a human would, of whether the surface is specular or specular enough.

In the case of another preferred embodiment in which the layer 12 is of glass or glassy material, the invention includes, among other methods, watching for the formation of a specular surface, just as in the case of a hard-metal layer. In the case of a glass layer 12, the process of becoming specular could involve covering the desired area of the blade with glass, softening the glass by heating, and watching for the formation of an image in the glass surface, indicating a specular surface.

In one preferred embodiment of that method, the glassy material 12, which is most preferably glass having a coefficient of thermal expansion close to that of the substrate 10, is reduced to fine dust or powder and sprinkled onto the substrate 10 in an oven. This will gradually build up a sufficient thickness to coat and fill the irregularities on the substrate. The point at which sufficient dust has fallen to create a specular surface will be apparent from the formation of a specular image.

One method of making the invention is to move a strip of substrate sheet metal through an oven and coat it with glassy material continuously. Alternatively, the strip can move through a plating solution and plate it with chromium or another hard metal, or through an electro-polishing bath. The coated sheet metal emerging from this process with a specular surface can then be coated with hard material or, if continuous coating is not possible because of vacuum or other requirements, it can be cut into pieces (preferably corresponding to a single blade), and those pieces are coated with the plate of hard material.

Figure 5:
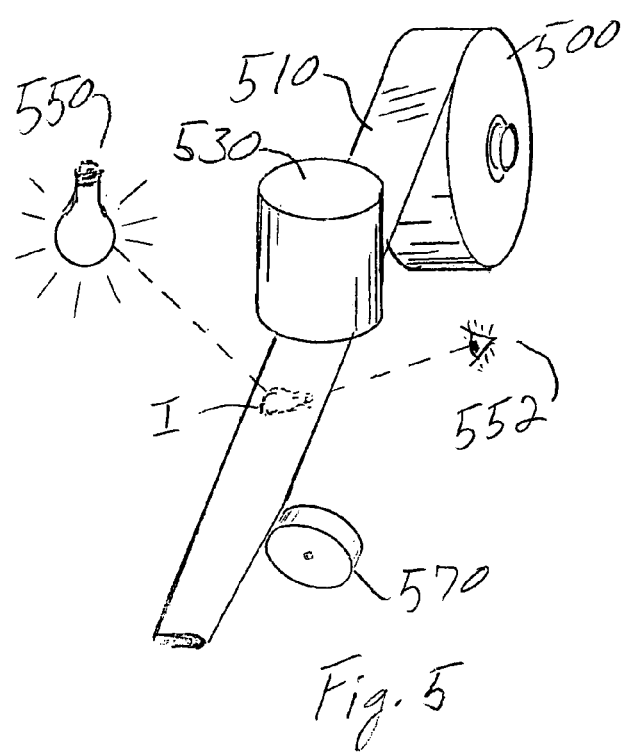
FIG. 5 is a perspective schematic view of a method of making the invention.

FIG. 5 illustrates in schematic form the processes discussed above, in which a strip 510 of material such as steel moves more-or-less continuously to a polishing device 530. The strip 510 may unroll from a coil 500. The device 530 polishes the strip 510 by some method such as mechanical polishing, electro-polishing, heating a glassy covering, chromium plating, or any other polishing process, at least on one side in the region adjacent to what will be the cutting edge.

A luminous object 550 is disposed in conjunction with a human eye or optical device 552 which detects the image I of the object 550 on the strip 510. Detection of the degree to which the strip 510 is specular, by the quality and/or intensity of the image I, provides feedback for the blade-making process.

Optionally, the strip 510 is folded over by a folding device shown schematically as a roller 570, which stiffens the blade as discussed below.

If possible, the hard layer 20 of FIG. 2 may be placed onto the specular surface continuously according to FIG. 5. For example, a knife with only a layer 12 of chromium, glass, or the like without any ceramic plate 20 could be made according to FIG. 5. However, in the embodiment of the invention in which ceramic layer 20 is laid over the specular surface, it is anticipated that it would be impractical to lay down the ceramic continuously because a high vacuum is needed.

The folded-over strip 510 is therefore preferably cut into lengths for individual blades, coated with ceramic, and sharpened.

The folding operation stiffens the blade. To further stiffen the blade, the interior space may be filled with an easily-abraded material such as plastic 600, shown in FIG. 6. This creates a "sandwich" or "stressed-skin" structure in which the outer layers (the strip 510) have a high tensile strength. This makes for a light but strong blade which is easily sharpened because the plastic 600 is soft and easily abraded.

The invention includes a graduated series of layers, progressively softer toward the interior. Preferably, the thickness of each layer increases progressively away from the cutting layer. The thickness may increase, for example, proportionally or exponentially with the order of the cutting layer. The reason for this is that a thin but hard layer needs support from an adjacent layer of equal strength, which means that an adjacent layer made of weaker material must be thicker to match the strength of the support layer closer to the cutting layer.

Figure 7:
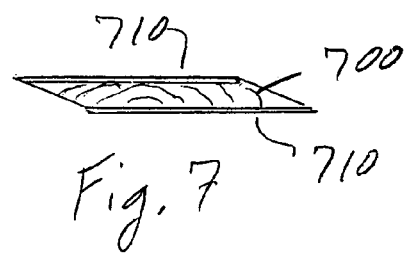
FIG. 7 is a cross-sectional view similar to FIG. 6 but showing an alternative embodiment.

FIG. 7 shows a knife blade with two outer layers 710 of sheet metal, for example, stainless steel, and a core 700 of wood, which might be fastened with epoxy.

The blades of FIGS. 6 and 7 combine outer layers with a hard edge (for example, stainless steel, chromium, glass, or ceramic) with a core material that is resistant to compression (that is what makes such a blade stiff, in combination with high tensile strength in the outer layers) and which is also easily abraded. This makes such a knife easy to sharpen.

When a blade is sharpened, the angle of the cutting edge should be maintained. This means that material must be removed for some distance back from the edge, which in turns means that a substantial amount of material must be removed. When that material is stainless steel, as in a conventional knife, the sharpening process involves a good deal of work and/or time.

Sharpening is a problem for most people, who do not have the proper knowledge or tools (such as sharpening stones and oil) for keeping their knives sharp. As a result, most homes have dull knives. Professional blade users usually have the tools and know-how to sharpen their blades, but must interrupt their work and spend inordinate amounts of time in sharpening. Razors, utility knives, and kitchen knives are customarily thrown out when dulled, which is wasteful, expensive, and creates bulky and dangerous trash. Blades made of very hard materials like sapphire and ceramic, though they remain sharp for an extended time, cannot be sharpened at all; eventually they too dull and are thrown out.

Preferably, the invention includes a core which is soft (easily abraded) but sufficiently resistant to compression, and outer layers that are hard and have high tensile strength. If the materials of the core and outer layers are dissimilar, they can be bonded. In general, hard materials are stiffer than soft materials; that is, they have a larger modulus of elasticity in tension. They also tend to have a higher tensile strength. For example, alloy steel is harder, stiffer, and stronger than aluminum, which in turn is harder, stiffer, and stronger than wood. Therefore it is not difficult to choose materials to make a blade stiff and also easy to sharpen.

Moreover, hard materials are often less dense than soft materials and therefore the blades of FIGS. 6 and 7 will also be light in weight.

The modulus of elasticity (elastic modulus or Young's modulus), in psi×10$^6$ in tension, for some materials is: steel 30, aluminum 10, and fir wood 1.76.

I claim:

1. A blade, comprising:
    a substrate including a specular surface, wherein at least some reflected image is visible on the surface; and
    a thin plate deposited on the specular surface, the plate comprising a plate material that is harder than the substrate;
    wherein the substrate is beveled toward a cutting edge of the blade; and
    wherein the cutting edge comprises the plate extending to the cutting edge on a single side of the blade;
    whereby the cutting edge is straight in a cutting direction.

2. The blade according to claim 1, wherein the substrate comprises
    a base portion including a first material and
    a surface portion including a second material that is harder than the first material and less hard than the plate material, wherein the surface portion comprises the specular surface.

3. The blade according to claim 2, wherein the second material comprises chromium.

4. The blade according to claim 2, wherein the second material comprises glass.

5. The blade according to claim 1, wherein the plate material comprises a ceramic.

6. The blade according to claim 1, wherein the plate has a thickness on the order of a micron.

* * * * *